(12) United States Patent
Aardsma

(10) Patent No.: US 10,863,764 B2
(45) Date of Patent: Dec. 15, 2020

(54) COMPOSITIONS AND METHODS FOR TREATING AGING AND/OR IMPROVING HUMAN HEALTH

(71) Applicant: Gerald E. Aardsma, Loda, IL (US)

(72) Inventor: Gerald E. Aardsma, Loda, IL (US)

(\*) Notice: Subject to any disclaimer, the term of this patent is extended or adjusted under 35 U.S.C. 154(b) by 0 days.

(21) Appl. No.: 16/025,209

(22) Filed: Jul. 2, 2018

(65) Prior Publication Data

US 2019/0000125 A1 Jan. 3, 2019

Related U.S. Application Data

(60) Provisional application No. 62/604,371, filed on Jul. 3, 2017.

(51) Int. Cl.
| | |
|---|---|
| *A61K 31/66* | (2006.01) |
| *A23L 33/15* | (2016.01) |
| *A61K 31/662* | (2006.01) |
| *A61K 9/00* | (2006.01) |
| *A23L 33/10* | (2016.01) |

(52) U.S. Cl.
CPC ............ *A23L 33/15* (2016.08); *A23L 33/10* (2016.08); *A61K 9/0095* (2013.01); *A61K 31/662* (2013.01); *A23V 2002/00* (2013.01); *A23V 2200/302* (2013.01); *A23V 2200/31* (2013.01); *A23V 2250/70* (2013.01)

(58) Field of Classification Search
CPC ...................................................... A61K 31/66
USPC ........................................................... 514/75
See application file for complete search history.

(56) References Cited

U.S. PATENT DOCUMENTS 4,016,264 A \* 4/1977 Clark .................... A61K 31/66
514/141

OTHER PUBLICATIONS

Gerald E. Aardsma, Aging Cause and Cure, Aardsma Research & Publishing, Aug. 2017, available at http://www.biblicalcronologist.org/products/Aging_book.php.
Preventing Animal Warts, Indiana State Board of Animal Health-Tech Bulletin RC4-11.98, available at http://www.state.en_us/boah/files/Animal%20Wart%20Prevention%2011-12.pdf.

\* cited by examiner

*Primary Examiner* — Raymond J Henley, III
(74) *Attorney, Agent, or Firm* — McCarter & English, LLP; Jonathan M. Sparks; Wendy Thai

(57) ABSTRACT

The invention provides a composition comprising methylphosphonic acid or a salt thereof for human consumption. The invention also provides a method for treating aging and/or improving health in a human. Methods of the invention involve providing or administering methylphosphonic acid or a salt thereof to a human in need thereof for consumption. The invention provides nutritional and pharmaceutical compositions and articles containing such compositions including, for example, a nutritional supplement, a beverage, a food substance, a prepackaged food or meal, or a nutraceutical, as well as a pharmaceutical.

22 Claims, No Drawings

COMPOSITIONS AND METHODS FOR TREATING AGING AND/OR IMPROVING HUMAN HEALTH

CROSS REFERENCE TO RELATED APPLICATIONS

This application claims priority to U.S. Provisional Patent Application No. 62/604,371, filed on Jul. 3, 2017, the content of which is incorporated herein by reference in its entirety.

BACKGROUND

It has been reported that physical decline associated with aging in humans occurs as early as the third decade of life. Body functions are believed to peak before age 30, which is then followed by a gradual and continuous decline. Besdine, R. W., Changes in the Body with Aging, MERCK MANUALS, Merck Sharp & Dohme Corp, 2018, available at www.merckmanuals.com/home/older-people%E2%80%99s-health-issues/the-aging-body/changes-in-the-body-with-aging (last visited Jun. 20, 2018).

Bone density in men and women, for example, begins to diminish from about age 30 and accelerates in women after menopause. Villa-Forte, Effects of Aging on the Musculoskeletal System, MERCK MANUALS, Merck Sharp & Dohme Corp, 2018, available at www.merckmanuals.com/home/bone,-joint,-and-muscle-disorders/biology-of-the-musculoskeletal-system/effects-of-aging-on-the-musculoskeletal-system (last visited Jun. 20, 2018). The decrease in bone density often leads to development of osteoporosis as the individual ages. The decrease in bone density is also accompanied by a similar and gradual loss of muscle mass and strength, which often leads to arthritis. See Villa-Forte.

Age-related loss of function occurs at the cellular level, as well as the level of the organs and body systems and affects not only the bones and muscles, but also the joints, body fat, the eyes, the ears, the mouth and nose, the skin, the brain and nervous system, the heart and blood vessels, the muscles involved in breathing, the lungs, the digestive system, the kidney and urinary tract, the reproductive system, the endocrine system, blood, and the immune system. See Besdine.

Thus, the decline in body functions has far reaching effects on individual health, sense of well-being, and quality of life.

SUMMARY

The invention relates to treating aging and/or improving health. The invention is based on the discovery that methylphosphonic acid (MePA) is an essential substance in the diet. More specifically, the invention is based on the discovery that aging and associated health decline and symptoms thereof are manifestations of a vitamin deficiency disease, in particular, a deficiency of MePA. Thus, the invention provides compositions and methods for treating aging and/or improving health. The invention provides compositions for human consumption that include MePA or a salt thereof and an ingredient acceptable for human consumption. The invention provides methods of use that involve providing or administering a composition that has MePA or a salt thereof and an ingredient acceptable for human consumption, as well as methods of use that involve providing or administering a nutritionally or pharmaceutically effective amount of MePA or a salt thereof.

In one aspect, the invention provides a composition for human consumption comprising methylphosphonic acid or a salt thereof and an ingredient acceptable for human consumption.

In one embodiment, the composition comprises from about 1 microgram to about 1 milligram of methylphosphonic acid or a salt thereof. In one embodiment, the composition comprises less than about 2.5 weight-% of methylphosphonic acid or a salt thereof. In one embodiment, the salt is a sodium, potassium, calcium or magnesium salt.

In one embodiment, the composition further comprises one or more vitamins.

In one embodiment, the composition is a chewable solid. In one embodiment, the composition is a liquid. In one embodiment, the composition is a beverage. In one embodiment, the composition is a nutritional bar.

In one embodiment, the composition is a nutritional composition wherein the ingredient acceptable for human consumption is generally regarded as safe.

In one embodiment, the composition is a pharmaceutical composition wherein the ingredient acceptable for human consumption is a pharmaceutically acceptable carrier. In one embodiment, the composition is formulated for topical or oral administration.

In another aspect, the invention provides a method for treating aging and/or improving health in a human in need thereof, the method comprising providing or administering a composition of the invention to the human for consumption thereby treating aging and/or improving health.

In one embodiment, the invention provides a method for treating aging and/or improving health in a human who has, has had, or is susceptible to an inflammatory disease, eczema, acne, headaches, or any combination thereof.

In another aspect, the invention provides a method for treating aging and/or improving health in a human in need thereof, the method comprising providing or administering a composition of the invention to the human thereby treating aging and/or improving health.

In another aspect, the invention provides a method for treating aging and/or improving health in a human in need thereof, the method comprising providing or administering methylphosphonic acid or a salt thereof to the human for consumption thereby treating aging and/or improving health.

In another aspect, the invention provides a consumable article comprising a composition of the invention, sealed packaging material within which the composition is disposed, and printed text comprising information pertaining to the composition, wherein the printed text is on the surface of the packaging material, on a label affixed to the packaging material, or provided as an accompanying insert of the article.

In one embodiment, the article is a beverage, wherein the sealed packaging material is a container effective to hold a liquid without leaking and within which the composition is disposed, wherein the composition is a beverage comprising methylphosphonic acid or a salt thereof.

In one embodiment, the article is prepackaged food.

In another aspect, the invention provides a composition for human consumption consisting essentially of methylphosphonic acid or a salt thereof and one or more ingredients acceptable for human consumption.

As used herein, the singular forms "a", "an", and "the" include plural reference unless the content clearly dictates otherwise.

As used herein, the term "about" in reference to a numeric value means within 10% of the specified value, i.e., within + or −10% of a reference value.

Any feature or combination of features described herein are included within the scope of embodiments of the present invention provided that the features included in any such combination are not mutually inconsistent as will be apparent from the context, this specification and the knowledge of one of ordinary skill in the art.

Unless otherwise defined, all technical and scientific terms used herein have the same meaning as commonly understood by one of ordinary skill in the art to which this invention belongs. In case of conflict, the present specification, including definitions, will control. In addition, the materials, methods, and examples are illustrative only and not intended to be limiting. Although methods and materials similar or equivalent to those described herein can be used to practice the invention, suitable methods and materials are described below.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

Other features and advantages of the invention will be apparent from the following detailed description and from the claims.

DETAILED DESCRIPTION

The invention relates to treating aging and/or improving health. The invention is based on the discovery that MePA is an essential substance in the diet. More specifically, the invention is based on the discovery that aging and associated health decline and symptoms thereof are manifestations of a vitamin deficiency disease, in particular, a deficiency of methylphosphonic acid (MePA). Thus, the invention provides compositions and methods for treating aging and/or improving health. The invention provides compositions for human consumption that include MePA or a salt thereof and an ingredient acceptable for human consumption. The invention provides methods of use that involve providing or administering a composition that has MePA or a salt thereof and an ingredient acceptable for human consumption, as well as methods of use that involve providing or administering a nutritionally or pharmaceutically effective amount of MePA or a salt thereof.

Methylphosphonic Acid

Methylphosphonic acid (MePA) refers to a compound of the formula $CH_3P(O)(OH)_2$. As used herein, the term "methylphosphonic acid" or "MePA" also includes methylphosphonate, the doubly negative ion resulting from loss of two protons from methylphosphonic acid, and hydrogen methylphosphonate, the singly negative ion resulting from loss of one proton from methylphosphonic acid.

The invention provides for the use of MePA, as well as salts thereof. Examples of salts of MePA include alkali metal or alkaline earth metal salts such as sodium, potassium, lithium, calcium, or magnesium salts thereof. Salts of MePA may be obtained using standard procedures well known in the art.

Compositions of the Invention

The invention provides compositions containing MePA or a salt thereof formulated for human consumption. The term "formulated for human consumption" or "for human consumption" means formulated with one or more ingredients acceptable for human consumption and/or formulated using materials permitted to come in contact with food or pharmaceuticals as determined by the FDA. The term "consume" or "consumption" includes ingestion, as well as systemic or topical use for dietary, nutritional or therapeutic purpose by a human individual. Examples of a composition of the invention that is formulated for human consumption include, for example, a beverage, a food product, a dietary or nutritional supplement, a nutraceutical, or a pharmaceutical composition for topical, oral, parenteral, or systemic administration to a human individual.

A composition of the invention formulated for human consumption is substantially free of a substance that is unsafe or toxic for human consumption. Substances that are unsafe or toxic for human consumption are known in the art and include ingredients not generally recognized as safe as determined by the US Food and Drug Administration (FDA), as well as ingredients such as food additives that are not approved for use in human beverages, human foods, human dietary supplements, nutraceuticals, or pharmaceuticals as known in the art. See, for example, 21 C.F.R. §§ 189. The term also includes ingredients that are present at levels that are not approved for its intended use as known in the art.

A composition of the invention is formulated for human consumption where it includes one or more ingredients acceptable for use in human foods, cosmetics, or pharmaceuticals. A composition of the invention formulated for human consumption can include food-grade ingredients, is prepared using known food-grade ingredients or materials, or is prepared using materials permitted to come in contact with food as determined by the FDA. A composition of the invention is also formulated for human consumption if it includes a cosmetic grade ingredient or a pharmaceutical grade ingredient such as a pharmaceutically acceptable carrier, is prepared using pharmaceutical-grade reagents or materials, which are known in the art, or is prepared using materials permitted to come in contact with pharmaceuticals. Thus, a composition of the invention is formulated for human consumption where it is formulated for human dietary, nutritional, cosmetic or therapeutic/pharmaceutical use.

A composition of the invention includes MePA or a salt thereof and at least one ingredient acceptable for human consumption. Ingredients acceptable for human consumption include FDA-approved additives or substances generally regarded as safe (GRAS), which are well known in the art. Ingredients that have GRAS status can be found in the FDA's GRAS Notice Inventor. This is accessible at www.accessdata.fda.gov/scripts/fdcc/?set=GRASNotices. A composition of the invention can include one or more ingredients that are used in human foods or are permitted for use in human foods as known in the art. See, for example, the FDA database *Everything Added to Food in the United States* (EAFUS), which is accessible at www.accessdata.fda.gov/scripts/fcn/fcnNavigation.cfm?rpt=eafusListing.

See also the database *Substances Added to Food Inventory*, which is provided by the FDA and accessible at www.accessdata.fda.gov/scripts/fdcc/?set=FoodSubstances. See also *The Codex General Standard for Food Additives* (GSFA, Codex STAN 192-1995), Adopted in 1995 with latest revision in 2016, CODEX ALIMENTARIUS, INTER- NATIONAL FOOD STANDARDS, which is accessible at www.fao.org/gsfaonline/index.html?print=true. A composition of the invention can also include one or more ingredients that are permitted for use in human dietary or nutritional supplements. See, for example, Dietary Supplement Label Database provided by the National Institutes of Health, Office of Dietary Supplements, which is available at the website https://ods.od.nih.gov/Research/Dietary_Supplement_Label_Database.aspx; see also Dietary Supplement Products & Ingredients, available at www.fda.gov/Food/DietarySupplements/ProductsIngredients/. See also *Premarket Notification for a New Dietary Ingredient*, Federal Register, Volume 62, No. 184.

A composition of the invention can be a dietary or nutritional supplement, it can be included with human food or a human food product, or it can be a pharmaceutical composition formulated to be administered topically, orally or parenterally, for example, by intravenous, intramuscular, topical or subcutaneous routes. A composition of the invention can be a liquid, a powder, or a solid formulated with one or more ingredients, for example and without limitation, a carrier, one or more food additives, one or more vitamins, a nutritional supplement or a food item, or a pharmaceutically acceptable carrier such as an inert diluent or carrier. A composition of the invention can be formulated as a vitamin, as a multi-vitamin, a beverage, a health drink, a nutritional bar, or any other pre-packaged food product in liquid, solid, or semi-solid form. A composition of the invention can be a freeze-dried, condensed, frozen or pasteurized food product to which a select amount of MePA or a salt thereof has been added.

A composition of the invention can be a hard or soft shell gelatin capsule, compressed into a tablet, or incorporated directly with food in the patient's diet. For oral administration, MePA or a salt thereof can be combined with one or more excipients and used in the form of ingestible tablets, buccal tablets, troches, capsules, elixirs, suspensions, syrups, wafers, and the like.

Tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. When the unit dosage form is a capsule, it can contain a liquid carrier, such as a vegetable oil or a polyethylene glycol. Various other materials such as coatings can be used to otherwise modify the physical form of the solid unit dosage form. Tablets, pills, or capsules, for example, can be coated with gelatin, wax, shellac or sugar and the like. A syrup or elixir can contain MePA or a salt thereof, sucrose or fructose as a sweetening agent, methyl and propylparabens as preservatives, a dye and flavoring such as cherry or orange flavor. Any material used in preparing any unit dosage form should be pharmaceutically acceptable and substantially non-toxic in the amounts employed.

MePA or a salt thereof can be incorporated into sustained-release preparations and devices. MePA or a salt thereof can be administered intravenously or intraperitoneally by infusion or injection. Solutions of MePA or a salt thereof can be prepared in water, optionally mixed with a nontoxic surfactant. Dispersions can also be prepared in glycerol, liquid polyethylene glycols, triacetin, and mixtures thereof and in oils. A composition of the invention can contain a preservative to prevent the growth of microorganisms.

Dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating MePA or a salt thereof in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, MePA or a salt thereof can be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Ingredients acceptable for human consumption that can be included in a composition of the invention include, in addition to MePA or a salt thereof, one or more of the following: a carbohydrate such as one or more sugars; vitamin A (e.g. retinyl palmitate); vitamin C (e.g. ascorbic acid and sodium ascorbate); vitamin D (e.g. cholecalciferol); vitamin E (e.g. dl-alpha-tocopheryl acetate); vitamin B-6 (e.g. pyridoxine HCl); folic acid; vitamin B-12 (cyanocobalamin); biotin; pantothenic acid (calcium d-pantothenate); iodine (e.g. potassium iodine); zinc (e.g. zinc chelate);

choline (e.g. choline bitartrate); inositol; calcium (e.g. tricalcium phosphate); phosphorus (e.g. tricalcium phosphate); sodium; sucrose; glucose syrup; gelatin; canola lecithin; citric acid; a food coloring agent including annatto extract, blueberry and carrot concentrates, and purple carrot juice; lactic acid; medium chain triglycerides; natural flavors and pectin; high fructose corn syrup; corn syrup; boysenberry juice; citric acid; xantham gum; cellulose gum; caramel color; salt; sodium benzoate and sorbic acid; sodium hexametaphosphate; iron; fiber and any combination thereof.

Useful dosages or single servings of MePA or a salt thereof can be determined by methods known to the art, e.g., observation of onset of physiological response, and measurement of unused dose excreted in the urine.

Generally, the concentration of MePA or a salt thereof in a liquid composition, such as a lotion, can be from about 0.1-25 weight-% or from about 0.5-10 weight-%. The concentration in a semi-solid or solid composition such as a gel or a powder can be about 0.1-5 weight-%, about 0.5-2.5 weight-%, or about 1-2 weight-%. The effective amount of MePA or a salt thereof can vary with the particular salt selected as well as the select route of administration, the intent of the use, the nature of the condition to be treated and the age and condition of the patient. The effective amount of MePA or a salt thereof can be at the discretion of the attendant physician or clinician.

In general, a suitable dose or serving will be in the range of from about 0.001 microgram/kilogram body weight to about 3 micrograms/kilogram body weight, e.g., from about 0.01 microgram/kilogram to about 0.3 microgram/kilogram of body weight per day.

MePA or a salt thereof can be conveniently administered in unit dosage form or in single serving containing, for example, about 0.010 microgram to about 1000 milligrams, conveniently about 0.1 microgram to about 100 milligrams, more conveniently, about 1 microgram to about 10 milligrams per unit dosage form or single serving, or about 10 microgram to about 1 milligram. MePA or a salt thereof can be conveniently administered in unit dosage form or single serving containing 0.1 microgram to 100 microgram, conveniently 1 microgram to 10 micrograms, most conveniently, 2 micrograms to 6 micrograms per unit dosage form or serving.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

A nutritional supplement, food product, or a pharmaceutical composition of the invention can contain any amount of MePA, for example, about 1E-9 wt-% to about 3.33E-9 wt-%. It can also contain about 0.100 microgram of MePA or a salt thereof, or about 0.2 microgram, about 0.4 microgram, about 0.8 microgram, about 1 microgram, about 10 micrograms, about 20 micrograms, about 30 micrograms, about 40 micrograms, about 50 micrograms, about 60 micrograms, about 70 micrograms, about 80 micrograms, about 90 micrograms, about 100 micrograms, or more than about 100 micrograms of MePA or a salt thereof. The amount of MePA or a salt thereof in a composition is selected such that an effective dosage level will be obtained.

A composition of the invention can be packaged as a single-unit dose, multiple unit doses, as a single serving or multi-unit servings in sealed packaging. Thus, the invention also provides articles, which includes a composition of MePA or a salt thereof disposed in sealed packaging such as a sealed pouch, a bottle, or other container as known in the art and discussed further below. Individual package or article can include printed text or material providing information related to ingredient(s), amount(s), dosage(s), indication(s) or contra-indication(s); directions for use, or any combination thereof. Additional articles can include a single-serving or multiple-serving beverage or food item to which a select amount of a composition of the invention has been added.

Methods of the Invention

The invention provides methods for treating aging and/or improving health in a human. As used herein, the term "treat" or "treating" in reference to aging means preventing aging and/or any associated health decline, delaying the onset of aging and/or any associated health decline, slowing or reducing the rate or progression of aging and/or any associated health decline, preventing further aging and/or any associated health decline, as well as reversing aging and/or any associated health decline, thereby curing aging and/or any associated health decline. The term "improve," "improving" or "improvement" as used in reference to human health means an improvement in the physical, mental and/or psychological health of an individual by any noticeable amount, as well as a cessation of further loss, decline or deterioration.

The term "aging" refers to a loss, decline or deterioration of any one or more body functions resulting in increasing debilitation and elderliness. Aging includes a deterioration in any one or more conditions of the body, as well as a development of one or more diseases or medical conditions and any associated effects or clinical symptoms that typically occur as a human individual advances in age.

The loss, decline or deterioration of one or more body functions with aging can take place at the cellular level, as well as the level of one or more organs or body systems and can be observed as a decline in physical, mental or psychological health including an individual's fitness or wellbeing. The loss, decline or deterioration of one or more body functions can increase the propensity for physical injury, increase susceptibility to a disease such as an infectious disease, or accelerate development of a disease or medical condition to which an individual is predisposed. Thus, the disease can be an acquired disease such as an infectious disease, a disease or medical condition that the individual is predisposed to developing, or a congenital disease or medical condition. Non-limiting examples include, without limitation, chronic headaches, migraine headaches, eczema, acne, or other inflammatory condition. Thus, "health decline" includes a decline in any one or more body functions, the onset of a disease or medical condition, the worsening or progression of an existing disease or medical condition, as well as a decline in physical, mental or psychological health, fitness or wellbeing.

Thus, MePA or a salt thereof, and compositions of the invention that contain MePA or a salt thereof along with an ingredient acceptable for human consumption, can be used as a nutritional, dietary, or health supplement; as a cosmetic composition; or as a therapeutic composition to treat aging and/or any associated health decline including, for example, headaches including chronic headaches as well as migraine headaches; insomnia or other sleep disturbances; eczema, acne or other skin condition or irritation; inflammation; or injuries.

MePA or a salt thereof, and compositions of the invention that contain MePA or a salt thereof and an ingredient acceptable for human consumption, can be used to improve health of an individual by, for example, strengthening the immune system, promoting healing, improving mental faculties, and improving fitness or wellbeing.

The methods of the invention involve providing or administering to an individual in need thereof MePA or a salt thereof. The method of the invention also involves providing or administering to an individual in need thereof a composition of the invention that contains MePA or a salt thereof and an ingredient acceptable for human consumption. The composition can be a beverage, a food item, a dietary supplement in the form of a vitamin or multivitamin, or a pharmaceutical composition such as a tablet, pill, cream, ointment, or injectable. The methods of the invention can include identifying an individual in need of treatment for aging or improved health and providing or administering to the individual MePA, a salt thereof, or composition of the invention. An individual in need of treatment for aging or improved health can be identified based on age (e.g. typically 30 years old or above), or based on a loss, decline or deterioration of one or more body function and its associated effects or symptoms as described herein including, without limitation: (1) development of one or more diseases or medical conditions; (2) an increase in the propensity for physical injury; (3) an increase in susceptibility to a disease; (4) an acceleration or worsening of a disease or medical condition to which an individual is predisposed; and (5) a decline in physical, mental or psychological fitness or wellbeing.

Articles of the Invention

The invention also provides articles in the form of packaging within which MePA, a salt thereof, or a composition comprising MePA or a salt thereof are disposed that can be conveniently provided to a human individual for consumption. The article can be, for example and without limitation, a sealed pouch containing a single unit dose or single serving of MePA, a salt thereof, or a composition of the invention; a bottle containing multiple, single unit doses of MePA, a salt thereof, or a composition of the invention in chewable form; a beverage contained within a leak-proof container such as a glass bottle, a can or a box container known in the art for holding a fluid; a pre-packaged food product in which a food or meal fortified with MePA, a salt thereof, or a composition of the invention is contained in a microwaveable or oven-proof sealed tray that optionally may be packaged in a box; or a can food item in which the food or meal contained within is fortified with MePA, a salt thereof, or a composition of the invention.

Articles of the invention include printed text pertaining to the contents of the article. Printed text can be on the packaging material, e.g. printed on an exterior surface of the packaging material, on a label affixed to the packaging material, or on an accompanying label insert. The printed text can include any information pertaining to MePA, a salt thereof or a composition of the invention that may be useful to the individual in need thereof including, without limitation, the ingredient(s) contained within, quantities thereof, recommended dosage(s), indicator(s) or contraindicator(s) thereof, and/or directions of use thereof.

The foregoing description and following examples are intended to illustrate and not limit the scope of the invention defined by the scope of the claims.

EXAMPLES

Example 1

Methylphosphonic Acid (MePA) and Salts and Compositions Thereof

MePA [CAS Number 993-13-5; Linear Formula $CH_3P(O)(OH)_2$; Molecular Weight 96.02] is commercially available. MePA was obtained from MilliporeSigma (formerly Sigma-Aldrich) (product number 289868). A dietary supplement of 2 micrograms of MePA per day was prepared as follows. A solution containing 0.0040 grams of MePA in 100 milliliters of distilled water was prepared in a dropper bottle. This solution contained 2 micrograms of MePA per 50 microliters of water. Fifty microliters is the approximate volume of a drop of water. A drop of said solution was dispensed from said dropper bottle into a drinking cup and the cup was filled with drinking water to produce a once per day dietary supplement of MePA of about 2 micrograms.

Example 2

Safety of MePA Supplementation

There is no known risk to health, from either theory or experiment, due to inclusion of MePA in the diet in microgram per day amounts. Low toxicity is normal for the water-soluble vitamins. Safety of MePA is theoretically assured by the smallness of the daily dose and the water solubility of MePA. Toxicity studies in human volunteers and in animals have revealed no signs of any toxicity, even at very large doses.

MePA highly dissociates at physiological pH based on its pKa values ($pKa_1$=2.12 and $pKa_2$=7.29) and does not bioaccumulate. Because MePA is water soluble, excess MePA is rapidly eliminated from the body by the kidneys.

The low dosage of MePA combined with MePA's rapid elimination from the body in the urine makes expectation of toxicity unreasonable. The effect of the smallness of the dose is illustrated by comparison to the deadly synthetic compound sarin, which is used as a chemical weapon due to its extreme potency as a toxic nerve agent. A single dose of 500 micrograms (at least a factor of 10 above a reasonable daily vitamin MePA supplementation dose rate) administered to a healthy male volunteer, caused only "mild symptoms of intoxication." [https://en.wikipedia.org/wiki/Sarin.]

Seven months of supplementation of the diets of 36 ICR (Harlan) female mice at 100 mg MePA/liter in their drinking water beginning at 5.7 months of age yielded no symptoms of toxicity. This is equivalent to human MePA supplementation at roughly 250,000 micrograms of MePA per day.

Eight months of supplementation of the diets of two mature female cats at 2 micrograms MePA/day yielded no symptoms of toxicity. This is equivalent to human MePA supplementation at roughly 30 micrograms per day.

Eight months of supplementation of the diets of two mature male dogs at 10 micrograms MePA/day yielded no symptoms of toxicity. This is equivalent to human MePA supplementation at roughly 50 micrograms per day.

Human tests of MePA supplementation with 10 volunteers lasting at least five months for all volunteers and as long as thirty-one months for one volunteer, with doses in the range of 1 to 50 micrograms per day, yielded no symptoms of toxicity.

Example 3

Daily MePA Dietary Supplementation & Associated Health Benefits

MePA was administered as a dietary supplement to 10 pilot study volunteers. Testing was conducted in three phases: phase 1 involved a single volunteer participant; phase 2 included one additional volunteer, giving two participants total; and phase 3 included an additional eight volunteers, giving a total of ten participants. MePA doses varied, typically between 1 and 6 micrograms of MePA per day.

To objectify sleep experiences, which, early on, were observed to benefit from vitamin MePA supplementation, several participants were equipped with commercially available Fitbit Charge 2 bracelets. These devices automatically recorded activity and heart rate data, from which sleep stages were estimated by a Fitbit app on a daily basis. No negative side effects due to MePA supplementation were reported by any of the volunteers. Significant health benefits were reported in most instances. Recurrent observations across multiple volunteers, implying therapeutic action due to the MePA vitamin, included improved sleep, reduced pain, diminished headaches/migraines, more rapid healing, improved immune function, improved mental health, more youthful skin, increased energy, improved heart function, and decreased nocturia.

Participant A was a 60-year-old male diagnosed in his early 50's with chronic inflammatory demyelinating polyneuropathy (CIDP), an autoimmune disease in which the immune system attacks the myelin sheath surrounding nerves resulting in loss of nerve impulses to peripheral muscles, with ensuing weakness. At the time of diagnosis, Participant A had difficulty lifting his fork to feed himself, was unable to button his shirt or move a blanket, and was unable to walk up or down stairs unassisted. The symptoms of CIDP experienced by Participant A improved substantially though not completely with several standard treatment regimens including high prednisone, then IV-Ig, and finally 60 ml Hizentra home infusions twice per week.

Participant A received a daily supplement of MePA according the following dose history: (a) 1 microgram/day beginning Nov. 26, 2015; (b) 0 micrograms/day beginning Feb. 25, 2016; (c) 1 microgram/day beginning Feb. 28, 2016; (d) 0 micrograms/day beginning Mar. 5, 2016; (e) 1 microgram/day beginning May 5, 2016; (f) 0 micrograms/day beginning May 26, 2016; (g) 1 microgram/day beginning Jul. 18, 2016; (h) 0 micrograms/day beginning Aug. 15, 2016; (i) 1 microgram/day beginning Sep. 15, 2016; (j) 2 micrograms/day beginning Jun. 9, 2017; (k) 4 micrograms/day beginning Jul. 16, 2017; (l) 50 micrograms/day beginning Aug. 12, 2017; (m) 0 micrograms/day beginning Aug. 25, 2017; (o) 6 micrograms/day beginning Aug. 26, 2017; (p) 4 micrograms/day beginning Dec. 30, 2017; (q) 8 micrograms/day beginning Feb. 3, 2018; and (r) 6 micrograms/day beginning Mar. 12, 2018. Participant A experienced no adverse side effects from MePA supplementation.

With MePA supplementation at 1 microgram/day, Participant A reported positive health effects at three and a half weeks. Participant A reported an improvement in leg muscle strength and stamina. Prior to treatment, the participant was able to walk one mile a day; this distance increased to two miles a day after three and a half weeks of MePA supplementation. After five and a half weeks of treatment, Participant A could forgo the biweekly infusions for CIDP without noticeable loss of muscle strength or stamina. The positive health effects and improvement of CIDP had not diminished as of the final report, nearly two and a half years after MePA supplementation began. Additional health benefits associated with MePA supplementation reported by Participant A included improved sleep, less frequent headaches and migraines, more rapid healing, enhanced immune function, more youthful skin, decreased sensitivity to cold, improved circulation and increased psychological energy. The following specific health benefits were reported by Participant A:

Improved sleep as evidenced by sleep being deeper and less interrupted, resulting in less sleep needed and feeling more rested;

Less frequent headaches and migraines, declining rapidly from a once-every-two-weeks occurrence frequency to almost no occurrence of headaches or migraines for several months;

More rapid healing as evidenced by a quick cessation of muscle pain in the back and between shoulder blades due to heavy lifting, rapid healing of swollen, blistered and sprained finger and wrist, and rapid healing of a second-degree burn;

Enhanced immune function as evidenced by a clearing up of a chronic skin infection 13 months after MePA supplementation began, a decline in frequency of upper respiratory infections, and cessation of asthma-like symptoms that had been increasing for several years prior to MePA supplementation;

More youthful skin as evidenced by less skin dryness and rash in response to hot water exposure, diminished eczema, replacement of thickened and/or numb areas on the skin with skin of normal thickness and sensation, decline in cracked skin, and recession of spider veins on feet and ankles;

Improved circulation as evidenced by decreased sensitivity to cold and better temperature control of extremities; and Improvement in psychological energy as evidenced by ability to maintain the resolve needed to successfully lose excess weight.

Participant B was a 61-year-old female in good health who experienced chronic sleep trouble. Participant B received a daily supplement of MePA according to the following dose history: (a) 1 microgram/day beginning Nov. 7, 2016; (b) 2 micrograms/day beginning Jun. 9, 2017; (c) 4 micrograms/day beginning Aug. 3, 2017; (d) 50 micrograms/day beginning Aug. 12, 2017; (e) 0 micrograms/day beginning Aug. 25, 2017; (f) 6 micrograms/day beginning Aug. 26, 2017; (g) 4 micrograms/day beginning Dec. 30, 2017; (h) 8 micrograms/day beginning Feb. 3, 2018; and (i) 6 micrograms/day beginning Mar. 12, 2018 Participant B experienced no adverse side effects from MePA supplementation.

With MePA supplementation at 1 microgram/day, Participant B reported positive health effects at three weeks. Participant B highlighted improved sleep as the greatest health benefit. Prior to treatment, the participant had slept poorly most nights and had gotten up most mornings feeling fatigued and unable to cope with the day ahead. Sleep improved after three weeks of MePA supplementation. Participant B reported feeling refreshed and rested and able to handle the normal stress and workload of life. Additional health benefits associated with MePA supplementation reported by Participant B included reduced pain, improved mental health, more youthful skin, and diminished arthritis. The following specific health benefits were reported by Participant B:

Reduced pain as evidenced by relief from chronic hip pain, chronic neck pain, and arthritic pain in finger joints;

Improved mental health as evidenced by more positive attitude, ability to cope, and a "can do" feeling;

More youthful skin as evidenced by fading of aging spots on her face; and

Diminished arthritis as evidenced by cessation of episodes of arthritic inflammation in finger joints, with lessened distortion of the fingers.

Participant C was a 70-year-old male in good health, diagnosed with biochemical recurrence of prostate cancer three years following radical prostatectomy. Participant C received a daily supplement of MePA as follows: (a) 2 micrograms/day beginning Jul. 17, 2017; (b) 4 micrograms/day beginning Jul. 23, 2017; and (c) 8 micrograms/day beginning Jan. 7, 2018. Participant C experienced no adverse side effects from MePA supplementation. Progression of Participant C's prostate cancer was monitored by medical professionals using TSA measurements. Following MePA supplementation at 2 micrograms/day for two months, progression of Participant C's prostate cancer slowed, as evidenced by both a formal statistical analysis and a simple exponential growth least squares regression model of his TSA measurements. Additional health benefits associated with MePA supplementation reported by Participant C included reduced pain and more rapid healing and more youthful skin. The following specific health benefits were reported by Participant C:

Reduced pain as evidenced by no pain from sunburn.

Rapid healing as evidenced by quick mending of a puncture wound to the palm of one hand; and More youthful skin as evidenced by cessation of chronic peeling of thickened skin on palms and soles following three months of MePA supplementation.

Participant D was an 85-year-old female who received a daily supplement of 2 micrograms/day of MePA beginning Aug. 29, 2017. Participant D experienced no adverse side effects from MePA supplementation. Prior to MePA supplementation, Participant D was visibly elderly, had difficulty standing up and getting around even with a walker, felt she had little time left to live, and had lost desire to do much of anything. These symptoms of old age began to reverse rapidly following MePA supplementation at 2 micrograms/day. Health benefits associated with MePA supplementation reported by Participant D included improved sleep, more rapid healing, improved mental health, improved heart function, increased strength, and reduced dysphagia. The following specific health benefits were reported by Participant D:

Improved sleep as evidenced by beginning to sleep soundly for the first time in years;

More rapid healing as evidenced by full restoration of her arm which had broken in a fall three years earlier, had felt weak, shrunken, and sometimes painful, but now felt normal and able to be used as previously, and as evidenced by greater resilience in two falls subsequent to beginning MePA supplementation, neither of which yielded any serious consequences and from both of which she recovered rapidly (same day);

Improved mental health as evidenced by greater initiative, renewed interest in life, rejuvenated mental acuity, feeling happier, less anxious, less depressed, more at peace and more relaxed, and also evidenced by cessation of medications for anxiety and depression, and also evidenced by restored creativity and desire to resume artistic crafts and painting;

Improved heart function as evidenced by reduced need of heart medication for atrial fibrillation;

Increased strength as evidenced by improved mobility, renewed ability to walk without walker or cane, and increased amount of walking each day;

Reduced dysphagia as evidenced by ability to eat without choking, sneezing, and difficulty swallowing.

Participant E experienced no adverse side effects from consuming a daily supplement of MePA as follows: 2 micrograms/day beginning Sep. 4, 2017 and 4 micrograms/day beginning Oct. 4, 2017. Participant E was a 59-year-old female experiencing heart failure. In April of 2016, following a long history of heart trouble, Participant E experienced two life-threatening ventricular fibrillation events within 24 hours. These were very damaging to her heart. An echocardiogram revealed that her heart was enlarging, following a path toward total heart failure. Recovery or improvement seemed impossible. The heart specialist was waiting to see how long the damaged heart could hold up before it declined enough to warrant a transplant. Against expectations, at her regular annual evaluation, two months following initiation of daily supplementation with MePA, Participant E's heart was found to no longer be declining and its enlargement was found to be somewhat decreased. Additional health benefits besides improved heart function associated with MePA supplementation reported by Participant E included improved sleep, reduced pain, more rapid healing, enhanced immune function, improved mental health, and more youthful skin. The following specific health benefits were reported by Participant E:

Improved sleep as evidenced by feeling more rested and by a reduction from 10+ hours of sleep needed per night before beginning MePA supplementation to eight hours or less a few months after beginning MePA supplementation;

Reduced pain as evidenced by relief of chronic front and back pancreatic pain;

More rapid healing as evidenced by "fantastic" (doctor's word) healing upon removal of stitches from a minor surgery incision on her hand (particularly significant since with diabetes and poor heart function, healing had been notoriously difficult);

Enhanced immune function as evidenced by a chronic yeast infection around her waist resolving;

Improved mental health as evidenced by greater wakefulness, clarity of mind, increased mental acuity, and more positive outlook;

More youthful skin as evidenced by lightening of age spots on the upper side of her forearms; and Increased energy as evidenced by cessation of overwhelming fatigue, and ability to do yard work and tend flower beds for the first time in fifteen years.

Participant F was a 63-year-old male in fair health who received a daily supplement of 2 micrograms/day of MePA beginning Sep. 11, 2017. Participant F experienced no adverse side effects from MePA supplementation. Health benefits associated with MePA supplementation reported by Participant F following five months of MePA supplementation included reduced pain, diminished headaches, more rapid healing, more youthful skin, increased energy, and improved heart function. The following specific health benefits were reported by Participant F:

Reduced pain as evidenced by a reduction in frequency of "pinched nerve" back pains and reduction in frequency and severity of hemorrhoid pain;

Diminished headaches as evidenced by a reduction in frequency of recurring "pinched nerve" headaches;

More rapid healing as evidenced by healing more quickly than expected from cuts and bruises;

More youthful skin as evidenced by healing of what Participant F believed to be a spot of (undiagnosed) skin cancer on his left cheek which had first appeared well over a year previously;

Increased energy as evidenced by eagerness to undertake strenuous wilderness hikes; and Improved heart function as evidenced by cessation of recurrent palpitations (fast beating).

Participant G was a 59-year-old female in good health, who received a daily supplement of 2 micrograms of MePA beginning Sep. 11, 2017. Participant G experienced no adverse side effects from MePA supplementation. Health benefits associated with MePA supplementation reported by Participant G following five months of MePA supplementation included reduced pain and more rapid healing. The following specific health benefits were reported by Participant G:

Reduced pain as evidenced by cessation of left heel pain which had persisted for some months; and More rapid healing as evidenced by a knee problem quickly resolving itself, which prior to MePA supplementation had caused a loss of work.

Participant H was the oldest pilot study participant. Participant H received a daily supplement of 2 micrograms of MePA beginning Sep. 28, 2017 and experienced no adverse side effects from MePA supplementation. Participant H, was an 88-year-old male in poor health. Participant H had recently been moved from a care facility to a private residence with relatives who took over his final care, as he was doing poorly and was not expected to live much longer. Participant H lived four months, significantly longer than expected, with MePA supplementation. Specific health benefits associated with MePA supplementation reported by Participant G's family care givers included increased strength and improved mental health.

Participant I was a 59-year-old female in good health who received a daily supplement of 2 micrograms of MePA beginning Oct. 2, 2017. Participant I experienced no adverse side effects from MePA supplementation. Health benefits associated with MePA supplementation reported by Participant I following six months of MePA supplementation included improved sleep, increased energy, lessened nocturia, and improved gastrointestinal function. The following specific health benefits were reported by Participant I:

Improved sleep as evidenced by Fitbit sleep records and verbal report;

Increased energy as evidenced by not feeling worn out so frequently;

Lessened nocturia as evidenced by fewer nighttime trips to the bathroom; and

Improved gastrointestinal function as evidenced by reduced frequency of constipation.

Participant J was a 62-year-old male with Mitochondrial Myopathy (MM). Participant J experienced no adverse side effects from MePA supplementation after consuming a daily supplement of MePA as follows: (a) 2 micrograms/day beginning Oct. 8, 2017; and (b) 0 micrograms/day beginning ca. Mar. 17, 2018. MM results from a genetic defect in mitochondrial DNA, impairing ATP synthesis. MePA supplementation is not expected to reverse genetic diseases such as MM, and no improvement in MM associated with MePA supplementation was observed during the brief five and a half month trial period. Health benefits associated with MePA supplementation reported by Participant J following five months of MePA supplementation included improved sleep, lessened nocturia, and reduced hypertension.

The above working examples involving Participants A-J provide a working model of the invention to date. These examples, taken collectively, showed aging in the process of being cured in a group of ten individuals in various stages of vitamin MePA deficiency disease (i.e. aging) and exhibiting various symptoms due to the disease, having begun treatment for the disease from as much as two years and seven months ago to as little as eight months ago, as of the time of writing. That this constitutes a valid working model of the invention is most easily seen by comparison to some traditional vitamin deficiency disease. Consider the cure of pellagra via dietary supplementation with nicotinic acid, for example.

Clinically advanced pellagra is rare in the U.S. today, but before the discovery of nicotinic acid in the latter half of the 1930s, pellagra was common in the southern states where corn was a major dietary stable. The following is a description from back at that time of the effects on pellagra patients of treatment with nicotinic acid.

A comprehensive report has been made by Spies, Bean, and Ashe, based on observations at the Cincinnati General Hospital, and the Hillman Hospital, Birmingham, Ala., on the nicotinic acid treatment of hundreds of cases of classic pellagra. It is stated that: "The administration of adequate amounts of nicotinic acid or one of its compounds is followed by the disappearance of many symptoms of the disease. Within 24 to 72 hours [1 to 3 days], the fiery redness and swelling of the tongue, gums, mouth, throat, and vagina subside, and the associated Vincent's infection disappears. Within 24 to 72 hours, nausea and vomiting cease, the increased salivation decreases, and bowel movements become normal. Abdominal distention, pain and discomfort disappear and, in most cases, the desire for food returns. The acute, fiery red erythematous [reddening of the skin, usually in patches] dermal lesions, in which the epithelium [thin tissue forming the outer layer of a body's surface] is intact, blanch within 48 hours after the administration of nicotinic acid, but where the continuity of the skin is broken and the lesions are moist, ulcerated, dry or pigmented, there seems to be no specific benefit. Perhaps the most dramatic response of the pellagrin to nicotinic acid therapy is the disappearance of the acute mental symptoms. These symptoms, varying from slight confusion to delirium and mania, disappear rapidly, often over night. The maniacal patients become calm and the confused patients, mentally clear. After therapy they become readjusted, and often have excellent insight and memory of their actions, ideas and surroundings during the psychotic period. Apathy and lassitude give way to interest." [*Physicians' Vitamin Reference Book*, third edition (New York: E.R. Squibb & Sons, January 1940), 46-47.]

Thus, treatment provided relief of diverse symptoms with no hint of any negative side-effects. This is the signature of a working model of a cure for a water-soluble vitamin deficiency disease. This signature is displayed by the working examples involving Participants A-J discussed above.

A major difference in the analogy between pellagra and aging is that pellagra develops relatively quickly on a deficient diet and resolves relatively quickly on a diet appropriately supplemented with nicotinic acid, while aging develops relatively slowly on a deficient diet and resolves relatively slowly on a diet appropriately supplemented with methylphosphonic acid. Fortunately, however, some of the symptoms of aging begin to resolve rapidly, and because of this, the above working examples involving Participants A-J collectively furnish an easily identified working model of early stage of treatment in the cure of aging via dietary supplementation with MePA.

Participants A-J display a relief of diverse symptoms with no hint of any negative side-effects. Analogous to the report on the nicotinic acid treatment of pellagra cases quoted above, administration of adequate amounts of methylphosphonic acid is followed by the disappearance of many symptoms of the disease. Within a few weeks to a few months, the sleep disorders characteristic of aging subside. For example, there is less trouble getting to sleep (i.e., reduced insomnia), sleep is deeper and more refreshing, and less sleep is needed. Associated fatigue is reduced or disappears. The rate of wound healing is remarkably increased, and accompanying inflammation and pain is decreased. The incidence of headaches and migraines is reduced. Within a few weeks to a few months, diseases which have taken hold because of agedness, such as heart failure, cancers, and autoimmune disease, may begin to be slowed, reversed, or cured. Numerous skin disorders disappear. For example, skin becomes more moist and supple, chronic skin infections begin to clear up within a month after the administration of methylphosphonic acid, and aging spots begin slowly to fade. Perhaps the most dramatic response of the elderly to methylphosphonic acid therapy is the disappearance of chronic mental symptoms. These symptoms, varying from brain fog to depression and anxiety, disappear rapidly, sometimes within the first week. The depressed become more happy, the anxious, more calm, and the brain fogged, mentally clear. Apathy and lassitude give way to interest and creativity.

Participants A-J reported the relief of diverse symptoms with no hint of any negative side effects, which is the signature of a working model of the cure for a water-soluble vitamin deficiency disease. Thus, working examples provided by Participants A-J comprise a contemporary working model of the invention.

Example 4

Preconception Use of MePA Supplementation

A woman supplements her diet with MePA on a daily basis as described above. A child is conceived and born to the woman. Once the child is weaned, the child's diet is appropriately supplemented with MePA on a daily basis for the rest of the child's life. The child grows to adulthood, acquiring a youthful adult body which persists without aging.

What is claimed is:

1. A composition for human consumption comprising methylphosphonic acid or a salt thereof and an ingredient acceptable for human consumption, wherein the composition for human consumption is suitable for ingestion, suitable for systemic use, and/or non-toxic when used topically.

2. The composition of claim 1, which comprises from about 1 microgram to about 1 milligram of the methylphosphonic acid or a salt thereof.

3. The composition of claim 1, which comprises less than about 2.5 weight-% of the methylphosphonic acid or a salt thereof.

4. The composition of claim 1, wherein the salt is a sodium, potassium, calcium or magnesium salt.

5. The composition of claim 1, further comprising one or more vitamins.

6. The composition of claim 1, wherein the composition is a chewable solid.

7. The composition of claim 1, wherein the composition is a liquid.

8. The composition of claim 1, which is a beverage.

9. The composition of claim 1, which is a nutritional bar.

10. The composition of claim 1, which is a nutritional composition wherein the ingredient acceptable for human consumption is generally regarded as safe.

11. The composition of claim 1, which is a pharmaceutical composition wherein the ingredient acceptable for human consumption is a pharmaceutically acceptable carrier.

12. The composition of claim 11, which is for topical or oral administration.

13. A method for improving health in a human in need thereof, the method comprising providing or administering the composition of claim 1 to said human for consumption thereby improving health.

14. The method of claim 13, wherein the human has, has had, or is susceptible to an inflammatory disease, eczema, acne, headaches, or any combination thereof.

15. A method for improving health in a human in need thereof, the method comprising providing or administering the composition of claim 11 to said human for consumption thereby improving health.

16. A consumable article comprising the composition of claim 1, sealed packaging material within which the composition is disposed, and printed text comprising information pertaining to the composition, wherein the printed text is on the surface of the packaging material, on a label affixed to the packaging material, or provided as an accompanying insert of the article.

17. The article of claim 16, which is a beverage, wherein the sealed packaging material is a container effective to hold a liquid without leaking and within which the composition is disposed, wherein the composition is a beverage comprising methylphosphonic acid or a salt thereof.

18. The article of claim 16, which is prepackage food.

19. A composition for human consumption consisting essentially of methylphosphonic acid or a salt thereof and one or more ingredients acceptable for human consumption, wherein the composition for human consumption is suitable for ingestion, suitable for systemic use, and/or non-toxic when used topically.

20. A composition for human consumption comprising methylphosphonic acid or a salt thereof and one or more ingredients acceptable for human consumption, wherein the composition for human consumption is suitable for ingestion or systemic use by a human individual.

21. A method for improving health in a human in need thereof, the method comprising providing or administering the composition of claim 20 to said human for consumption thereby improving health.

22. A method for improving health in a human in need thereof, the method comprising providing or administering the composition of claim 19 to said human for consumption thereby improving health.

* * * * *